(12) United States Patent
Horvath et al.

(10) Patent No.: US 8,211,043 B2
(45) Date of Patent: Jul. 3, 2012

(54) METHOD OF CAREGIVER ASSISTING A PERSON IN NEED OF ASSISTED MOBILITY AND BELTED APPARATUS WITH MULTIPLE HANDLES

(75) Inventors: Mario Horvath, Palm Desert, CA (US); Jack Khorsandi, Hollywood, CA (US)

(73) Assignee: Grip-N-Ride, LLC, Hollywood, CA (US)

( * ) Notice: Subject to any disclaimer, the term of this patent is extended or adjusted under 35 U.S.C. 154(b) by 78 days.

(21) Appl. No.: 12/854,823

(22) Filed: Aug. 11, 2010

(65) Prior Publication Data

US 2011/0270144 A1 Nov. 3, 2011

Related U.S. Application Data

(63) Continuation-in-part of application No. 12/769,518, filed on Apr. 28, 2010.

(51) Int. Cl.
*A61F 5/00* (2006.01)

(52) U.S. Cl. ............... 602/19; 5/81.1 T; 2/312; 119/856

(58) Field of Classification Search .......... 128/845–846, 128/869, 876; D24/190; 119/856, 792; 224/160, 224/163; 602/19; 5/81.1 T; 2/44–45, 308, 2/311–312, 319; 414/921

See application file for complete search history.

(56) References Cited

U.S. PATENT DOCUMENTS 5,349,706 A * 9/1994 Keer ................................. 2/300
5,497,923 A * 3/1996 Pearson et al. ................ 224/639

* cited by examiner

*Primary Examiner* — Patricia Bianco
*Assistant Examiner* — Camtu Nguyen
(74) *Attorney, Agent, or Firm* — Cislo & Thomas, LLP

(57) ABSTRACT

A stabilizing belt for use by a person in need of assisted mobility, the stabilizing belt comprising a pad, a belt to wrap around the pad and secure the pad to a wearer, and a pair of handles attached to the pad. The pad may be uniquely contoured to provide support and comfort for the wearer, either the caregiver or the person in need of assisted mobility. A strap may be provided for added security and comfort. The belt may further comprise handle supports for reinforcement, a cover for durability, and a pocket for versatility.

19 Claims, 6 Drawing Sheets

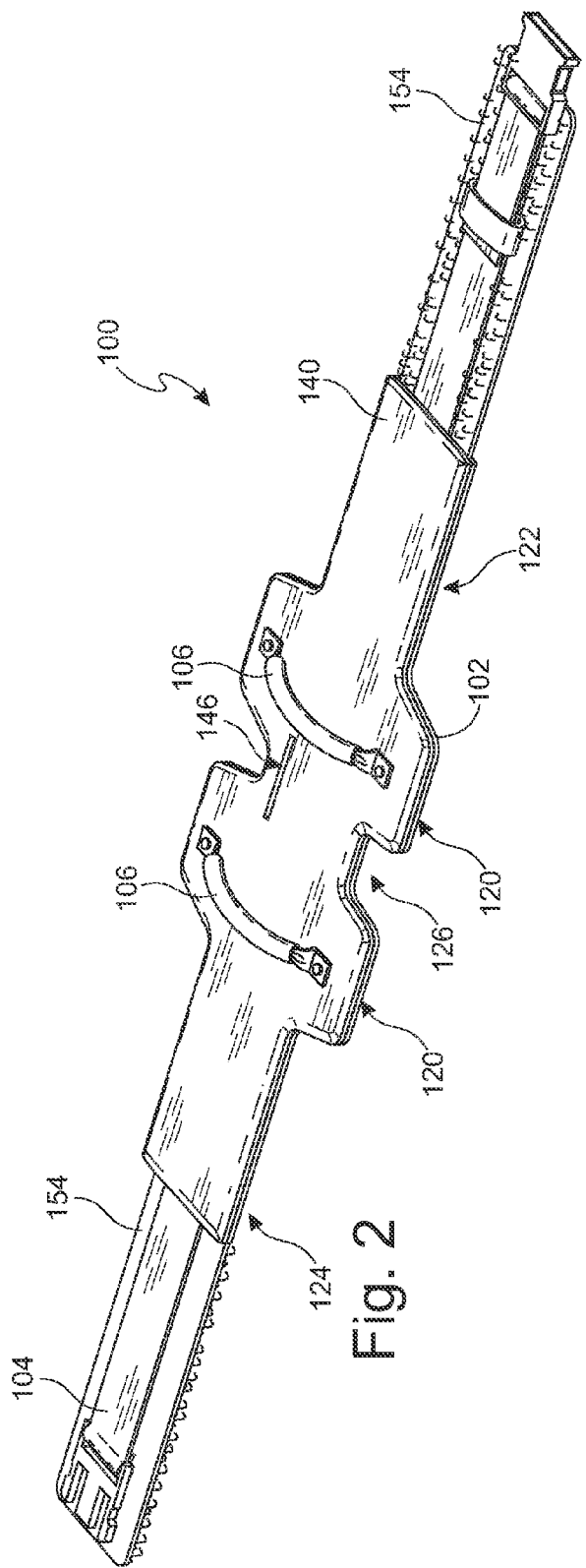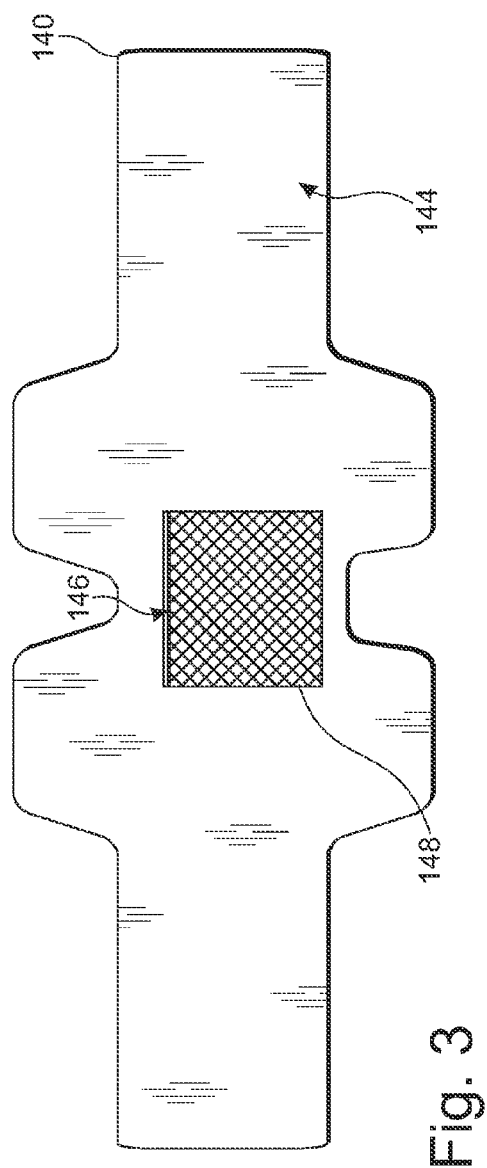

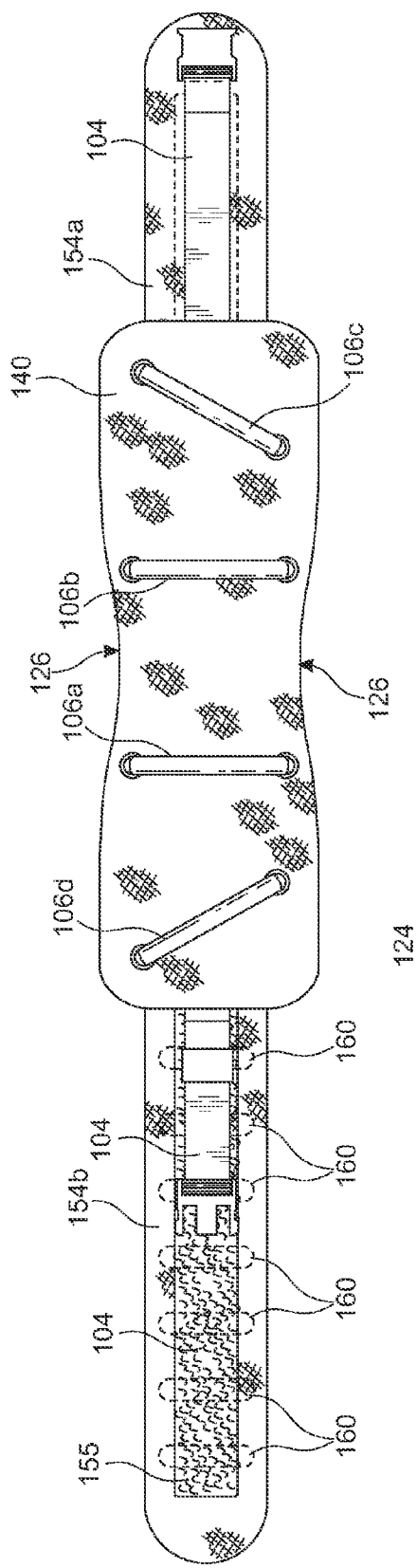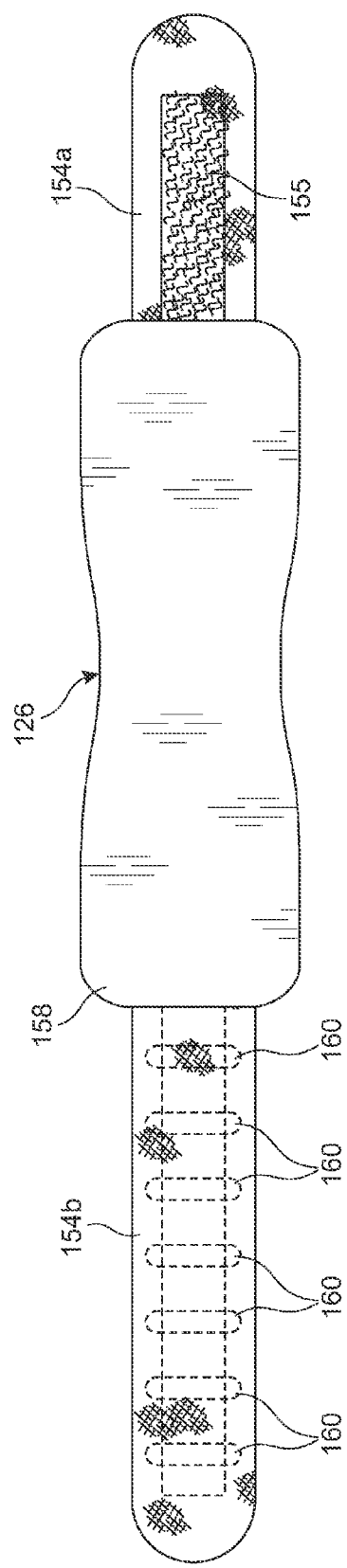

METHOD OF CAREGIVER ASSISTING A PERSON IN NEED OF ASSISTED MOBILITY AND BELTED APPARATUS WITH MULTIPLE HANDLES

CROSS-REFERENCE TO RELATED APPLICATION

This patent application is a continuation-in-part application of U.S. patent application Ser. No. 12/769,518, filed Apr. 28, 2010, which application is incorporated in its entirety here by this reference.

TECHNICAL FIELD

This invention relates to a support belt or stabilizing belt.

BACKGROUND

There are various modes of transportation in which two or more people may ride in tandem. For example, riding motorcycles, watercraft vehicles, all-terrain vehicles (ATV), snowmobiles, horseback riding, bicycles, or skiing are circumstances in which two or more people may be riding in tandem. In such situations, the back rider may hold onto the front rider in various uncomfortable and restricting ways to stabilize or balance himself or herself. In addition, current stabilizing belts are too cumbersome and, therefore, lack the versatility to be used across different activity, lack proper lumbar support, and are uncomfortable as the belt dig into the wearer's body.

Other circumstances may require the ability to stabilize the wearer of the belt, such as medical assistance and therapy. These belts also tend to be cumbersome and lack lumbar support. In addition, it is inconvenient, uncomfortable, and problematic to have an individual already in a weakened state to be forced to where a belt or vest so as to be assisted in movement.

For the foregoing reasons there is a need for an improved stabilizing belt that is versatile enough to be used across various activities, provide adequate lumbar support, is comfortable to wear, and easy to use for those requiring assistance for movement.

SUMMARY

The present invention is directed to a stabilizing belt that can be used for a variety of activities, provides adequate lumbar support, is comfortable to wear, and easy to use for those requiring assistance, such as medical assistance. One aspect of the present invention is to provide a stabilizing belt designed to provide adequate lumbar support yet provide flexibility for movement.

Another aspect of the present invention is to provide a stabilizing belt in which the fastening mechanism does not dig into the wearer and cause discomfort.

Another aspect of the present invention is to provide a stabilizing belt that can be used across various activities as opposed to a single activity.

Another aspect of the present invention is to improve the functionality of a stabilizing belt.

Another aspect is to provide assistance to those having difficulty with movements, such as a patient, without requiring the patient to don any additional equipment or device.

BRIEF DESCRIPTION OF DRAWINGS

FIG. 2 shows a perspective view of an embodiment of the present invention;

FIG. 3 shows an embodiment of the interior side of the cover;

FIG. 6 shows a plan view of the exterior side of an embodiment of the present invention;

FIG. 7 shows a plan view of the interior side of an embodiment of the present invention.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1:
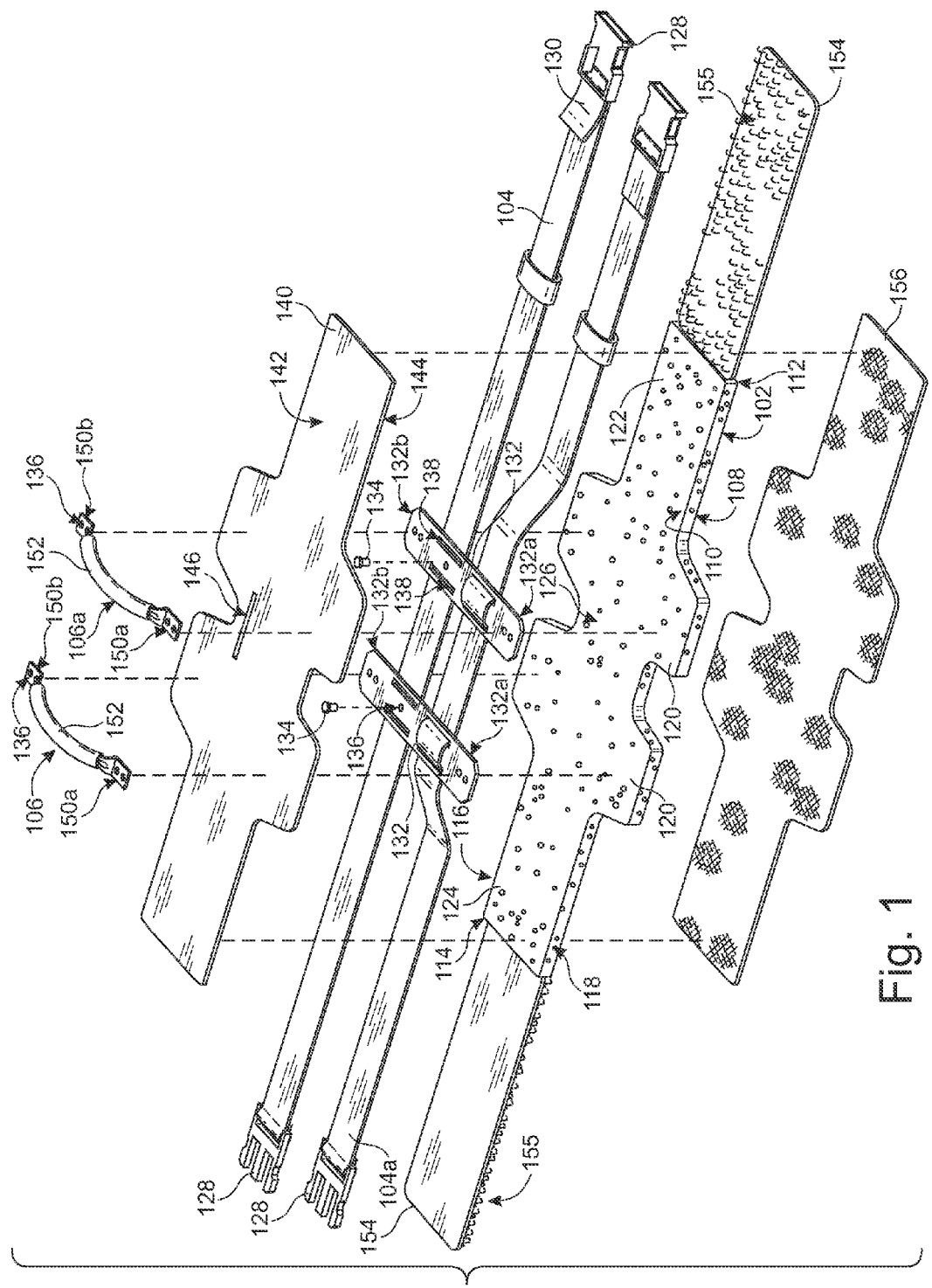
FIG. 1 shows an exploded view of an embodiment of the present invention.

With reference to FIGS. 1 and 2, the present invention is directed towards a stabilizing belt 100 for use, for example, by a pair of riders riding a vehicle, such as a motorcycle or watercraft, in tandem. The stabilizing belt 100 worn by the front rider provides a means for the back rider to stabilize himself or herself during the ride. In other uses, such as for medical assistance, the stabilizing belt 100 may be worn by the patient or the caregiver. In situations in which it is difficult for the patient to don the stabilizing belt 100 the caregiver can don the belt 100 providing the patient with multiple grasping points to find the best leverage.

The stabilizing belt 100 comprises a pad 102, a belt 104 to wrap around the pad 102 and secure the pad 102 to a wearer, and at least one handle 106 attached to the pad 102. The pad 102 provides support and comfort for the wearer. The belt 104 allows the pad 102 to be attached to the wearer. The handle 106 provides the means for the back rider, patient, or caregiver to stabilize himself or herself against the wearer.

The pad 102 comprises an interior side 108 that abuts the wearer, an exterior side 110 opposite the interior side 108, the interior and exterior sides 108, 110 defining a first edge 112, a second edge 114 opposite the first edge 112, a top edge 116 adjacent to the first and second edges 112, 114, and a bottom edge 118 opposite the top edge 116 and adjacent to the first and second edges 112, 114. The designation of the top and bottom edges 116, 118 has been made only for the sake of clarity and ease of discussion. Either edge can serve as the top or bottom depending on how the wearer wears the stabilizing belt.

Also, for the sake of clarity and ease of discussion the distance from the first edge 112 to the second edge 114 will be referred to as the length and the distance from the top edge 116 and bottom edge 118 will be referred to as the width. These designations apply to the other features of the present invention, such as the cover, strap, the mesh, and the like.

In some embodiments, the pad 102 may have a simple geometric shape. For example, the pad 102 may be rectangular, trapezoidal, oval, circular and the like. In some embodiments, the top and bottom edges 116, 118 of the pad 102 are uniquely contoured to provide better support, comfort, and versatility.

As shown in FIG. 1, in the some embodiments, the pad 102 comprises a lumbar support area 120 and bilateral side support areas 122, 124 that extend away from the lumbar support area 120 and terminate at the first and second edges 112, 114, respectively. The side supports 122, 124 may extend away from the lumbar support 120 in a uniform fashion, thereby forming a rectangular configuration. In some embodiments, the side supports 122, 124 may taper as they extend away from the lumbar support 120, thereby forming a triangular, trapezoidal, or oval configuration. In some embodiments, the width of the side support 122, 124 may expand rather than taper away from the lumbar support 120.

The lumbar support 120 occupies the middle portion of the pad 102. To enhance support given to the lumbar region of the wearer while minimizing weight of the stabilizing belt or discomfort to the wearer, the lumbar support 120 may be wider than the side supports 122, 124. In some embodiments, the lumbar support area 120 may be a single enlarged area extending from one side to the other side of the lumbar region of the wearer.

In some embodiments, to further add flexibility without compromising the support, the top and bottom edges 116, 118 within the lumbar support area 120 may converge toward each other at a central area 126. The central area 126 is the area that would be positioned along the spine of the wearer. Thus, the width of the central area 126 is less than the width of the lumbar support area 120. In such an embodiment, the lumbar support area 120 can be described as having two distinguishable or separate lumbar support areas 120, one for the left side and one for the right side of the wearer.

Due to the difference in width between the lumbar support areas 120 and the central area 126, the wearer is able to move and twist his or her body more freely as the central region 126 facilitates the twisting movement of the lumbar support areas 120 out of their natural plane.

Figure 4:
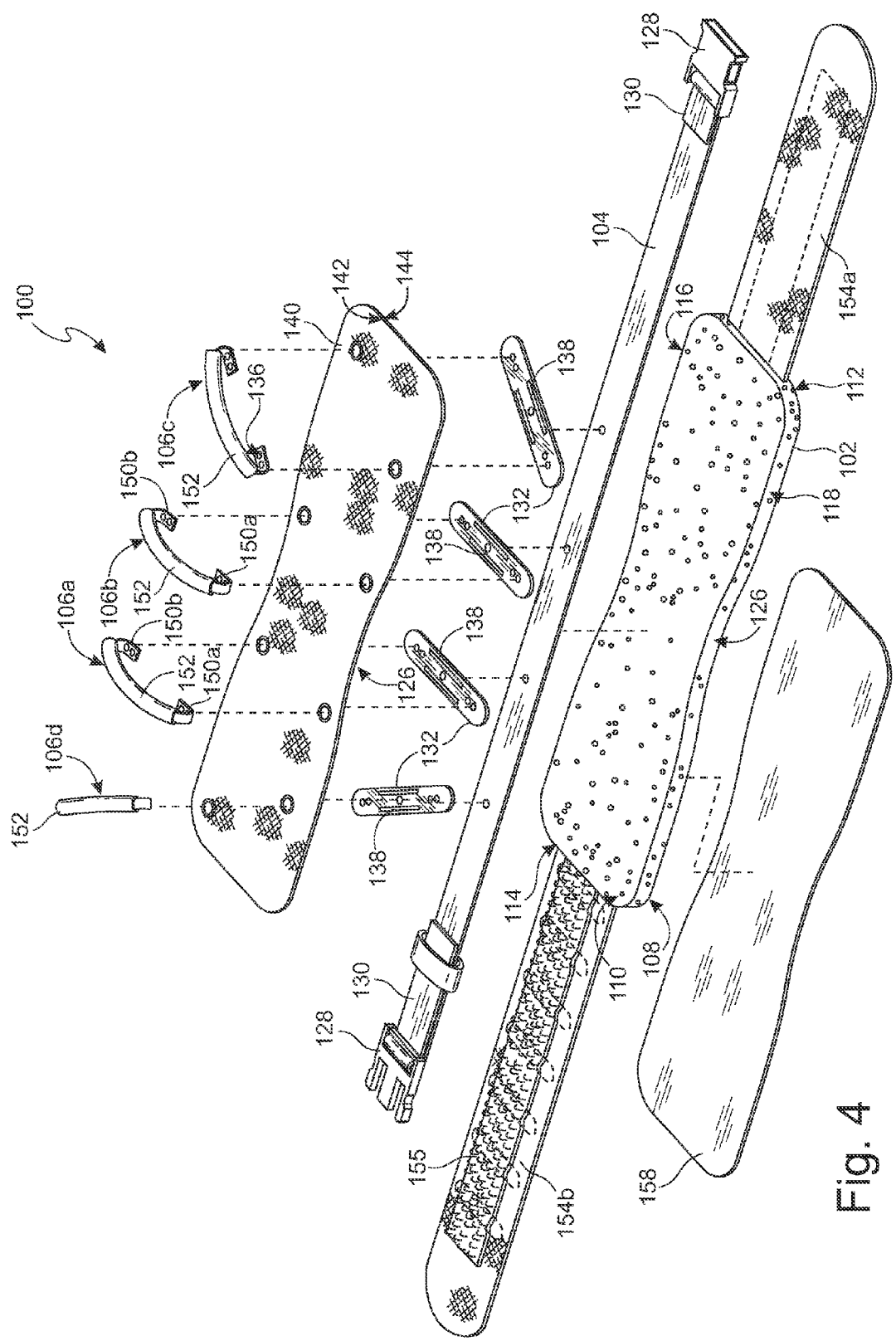
FIG. 4 shows an exploded view of another embodiment of the present invention.

As shown in FIG. 4, in some embodiments, the pad 102 may be generally rectangular in shape with the top and bottom edges 116, 118 tapering towards each other at the central area 126 of the pad 102. Therefore, the width at the central area 126 is generally smaller than the widths at the first and second edges 112, 114.

The pad 102 is generally flat and made of a cushion type material. Suitable materials for the pad 102 include foam, rubber, and variations thereof. In some embodiments, the interior side of the lumbar support area 120 may comprise a bulge. In other words, the surface of the interior side 108 on the lumbar support area 120 may be convex to match the curvature of the lumbar region of the spine of the wearer. This provides added support to the wearer.

To secure the pad 102 to the wearer, a belt 104 is provided to wrap around the pad 102 and the wearer. Preferably, since the belt 104 must withstand the pulling of the handles 106 by a second rider, a caregiver, a patient, and the like, the belt 104 should be made from a strong, generally inelastic material. For example, the belt 104 may be made of nylon, leather, canvas, or other sturdy fabrics, or materials that can be made sturdy. In some embodiments, additional belts 104a may be used to reinforce security and sturdiness.

The belt 104 further comprises a means for securing 128 the pad 102 to the wearer. The securing means 128 may be hook-and-loop fasteners, zippers, buttons, buckles, and the like. The belt 104 further comprises an adjustment strap 130 so that the belt 104 can be tightened or loosened before or after fastening.

In some embodiments, the belt 104 is fastened to the pad 102, preferably on the exterior side 110. In other embodiments, the belt 104 remains detached from the pad 102 relying on the frictional forces generated from tightening the belt 104 around the pad 102 for securement.

To improve the sturdiness and securement of the handles 106 to the pad 102, the handles 106 may be attached to handle supports 132. Handle supports 132 may be hard, thin sturdy pieces of plastic, metal, wood, composite material, or the like that is fastened to the pad 102 and the belt 104. In some embodiments, the handle supports 132 may have rounded and beveled edges. The force from pulling, twisting, and tugging of the handles 106 during use gets dispersed throughout the entire handle support 132 thereby minimizing damage to the pad 102. Otherwise, without the handle support 132, the force would be localized at the point of connection to the pad 102, which could easily damage the pad 102.

In the preferred embodiment, the handle supports 132 are irreversibly fastened to the pad with fasteners, such as rivets 134. As such, through-holes 136 may be provided on the handle supports 132 through which a rivet 134 may be inserted to fasten the handle support 132 to the pad 102. Additional through-holes 136 may also be provided to fasten the handles 106 to the handle support 132.

Other fastening means may also be used, such as stitching, adhesives, nuts and bolts, and the like. Irreversible fastening refers to fasteners that cannot be removed without noticeably damaging the fastener or the material to which the fastener is fastened. Reversible fasteners may also be used if it provides secure attachment without adding discomfort to the wearer.

Although the handle supports 132 may be attached anywhere on the pad 102, the preferred position is to attach the handle supports 132 to the lumbar support area 120 as shown in FIG. 2. In some embodiments, as shown in FIG. 4, multiple handles 106a-106d, and multiple handle supports 132a-132d may be used. The handles 102a-102d and handle supports 132a-132d can be positioned in a number of different strategic locations so as to maximize the function of the belt.

To facilitate the securement of the belt 104 to the pad 102, each handle support 132 may comprise a pair of elongated slits 138 through which the belt 104 can be interlaced as shown in FIG. 1 (the lower belt 104a). The slits 138 may be positioned at the opposite lateral edges of the handle support 132. In such an embodiment, the belt 104 may be attached to the pad 102 via the handle support 132 rather than being directly attached to the pad 102. Since the belt 104 is not directly fastened to the pad 102, this also allows the belt 104 to be adjusted to the left or to the right by adjusting the belt 104 through the slit 138. In embodiments utilizing multiple belts 104, multiple pair of slits 138 can be provided on the handle support 132 accordingly. Alternatively, each belt 104 can have a separate handle support 132.

In some embodiments, the stabilizing belt 100 may further comprise a cover 140 to conceal and protect the underlying components of the stabilizing belt 100. The cover 140 comprises an exterior side 142 and an interior side 144 opposite the exterior side 142. The interior side 144 of the cover 140 may be overlaid on top of the handle support 132, at least a portion of the belt 104, and the pad 102. In the preferred embodiment, the cover 140 has substantially the same shape as the pad 102 so as to fully cover the pad 102 while minimizing any excess material. In some embodiments, the cover 140 may completely cover or envelop the pad 102. In other embodiments, the cover 140 only covers the exterior side 110 of the pad 102.

In some embodiments, the cover 140 comprises a slit 146. On the interior side 144 of the cover 140 adjacent to the slit 146 may be a pouch 148. For example, if the slit 146 is a horizontal slit, a pouch 148 may be positioned just below the slit 146 so that the slit 146 and pouch 148 can function as a pocket. A user can insert various items through the slit 146 into the pouch 148.

The cover 140 may be made from any durable material, such as rubber, nylon, leather, canvas and other fabric material. In some embodiments, the cover 140 may be water proof or water resistant to keep the pad 102 dry for water sport activities.

The handles 106 may be attached through the exterior surface 142 of the cover 140 to the handle supports 132. Handles 106 may be made from hard, sturdy material such as metal, plastic, wood, and the like. The end portions 150a, b of the handles 106 can be riveted through the cover 140 onto the handle support 132 for secure attachment. In addition, the end portions 150a, b may be double stitched to the cover 140. The grip portion 152 of the handle 106 may be covered with foam or rubber to provide a comfortable grip.

In some embodiments, the handles 106 may be reversibly fastened to the handle supports 132. Utilizing reversible fasteners provides a means for adjusting the orientation or placement of the handles. By way of example only, the two handle supports 132 may be arranged parallel to each other a specified distance apart. Each handle 106 may be secured parallel to one handle support 132, thereby having a vertical orientation when the stabilizing belt 100 is worn. This allows the rear user to grasp the handles with his palms facing toward each other. To rearrange the orientation of the handles 106, the user can remove the fastener and re-fasten the handles 106 in a horizontal orientation, perpendicular to the handle supports 132 by fastening one of the end portions 150a of the first handle 106 to one end 132a of the first handle support 132 and the second end 150b of the first handle 106 to the same end 132a of the second handle support 132. The second handle 106a can be similarly fastened to the opposite end 132b of both handle supports 132. This allows the user to utilize a palm up or palm down grip.

In some embodiments, the handles 106, 106a and handle supports 132 may be configured to provide a means for adjusting the placement or orientation of the handle without having to disassemble the stabilizing belt. For example, the handle support 132 may be frame-shaped or be a single rectangular or square plate having slits and/or a plurality of holes. The ends 150a, 150b of the handles 106 may have retractable pins that can be retracted by the push of a button on the handles 106, 106a. In the retracted configuration, the handles may be free to slide along the slits and positioned at different holes. Release of the button allows the pins to engage the holes so as to be locked in place. This allows the user to change the distance between the handles 106, 106a or change the orientation and placement of the handles 106, 106a. In such an embodiment, the cover would also comprise slits or openings to allow the handles 106, 106a to move to a different position. Reversible fasteners that can be used in this embodiment include, but are not limited to nuts and bolts, magnets, suction cups, clips, spring loaded pins, bayonet-style connectors, mounts, and the like. In these embodiments, care should be taken so that the handles 106 do not slip out from the handle support 132 during use.

Figure 5:
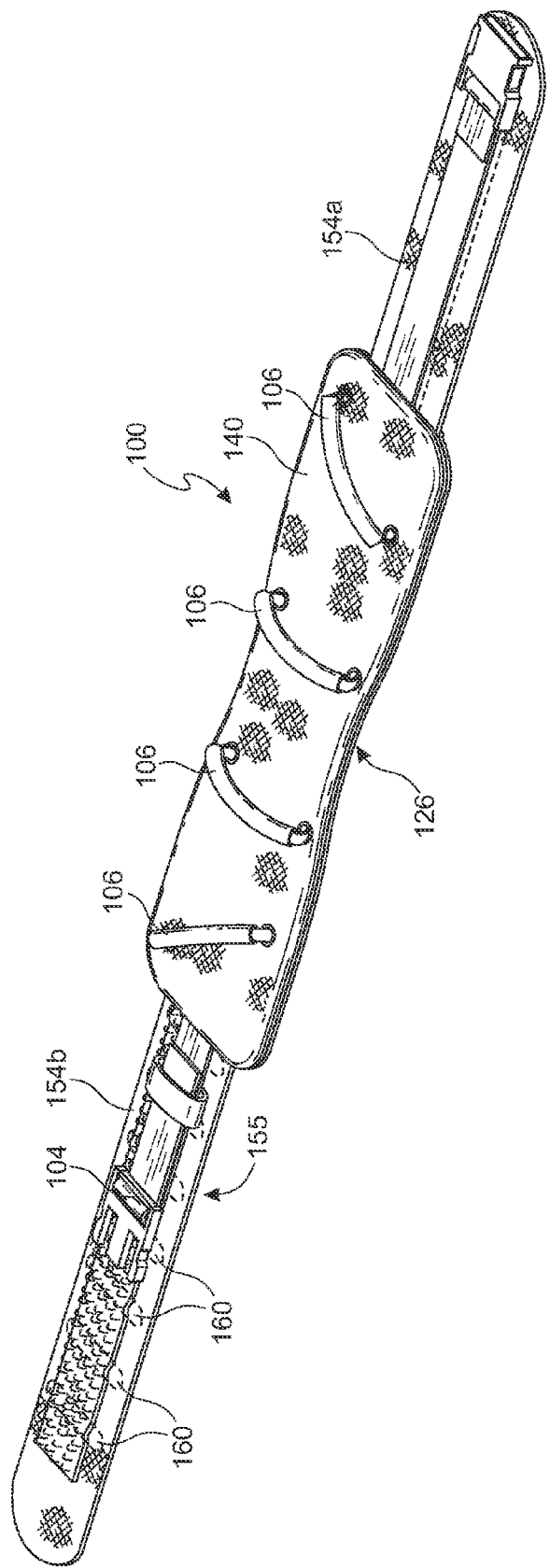
FIG. 5 shows a perspective view of the embodiment shown in FIG. 4 assembled.

In some embodiments, the stabilizing belt 100 may comprise a plurality of handles 106a-106d arranged in various configurations so as to provide the option of a variety of different grip positions without having to make any adjustments as shown in FIGS. 4 and 5. In addition, having a plurality of handles 106a-106d allows the user to change his or her grip instantly at any time. Handles 106a-106d may be arranged in a variety of positions, such as vertically, horizontally, at any oblique angle therebetween, and any combination thereof. Reference to the orientation of the handles is with respect to the wearer standing upright and the stabilizing belt being worn as intended. Each handle 106a-106d may have associated with it a handle support 132.

In another example, the stabilizing belt 100 may comprise four handles 106 arranged in a square or rectangular orientation. For example, a pair of horizontally oriented handles may be positioned at opposite ends of the vertically oriented handles 106.

In some embodiments, to facilitate securement of the pad 102 to the wearer, a strap 154 may extend out from each of the first and second edges 112, 114 of the pad 102. Preferably, the strap 154 may be an elastic material comprising a fastening means 155 so that the pad 102 and strap 154 can be wrapped around the wearer's body and fastened in the front, rear, or sides. For example, the strap 154 may comprise a fastening means 155, such as hook-and-loop fasteners, zippers, buttons, buckles, and the like. In some embodiments, the strap 154 may be a two piece strap, with the first piece attached to and extending from the first edge 112 and the second piece attached to and extending from the second edge 114. In some embodiments, the strap 154 may be one continuous piece that overlaps the entire pad 102. The one piece strap may be fastened to the pad 102. This allows the pad 102 to remain in place while the belt 104 securely fastens the pad 102 to the wearer.

The strap 154 also serves as an interface between the belt 104 and the wearer. This prevents the belt 104 from uncomfortably digging into the wearer's skin when the belt 104 is tightened around the wearer. To accommodate this function, the width of the strap 154 may be greater than the width of the belt 104. In embodiments comprising multiple belts 104 the width of the elastic strap 154 may be greater than the combined width of all of the belts and the spaces therebetween.

In embodiments having a two piece strap, as shown in FIG. 4, the first strap piece 154a may be elastic and the second strap piece 154b may be made of an inelastic fabric. The inelastic fabric material provides additional comfort and protection from the belt 104. The first strap piece 154a and the second strap piece 154b may have fastening means 155 to fasten the first strap piece 154a to the second strap piece 154b. For example, the first and second strap pieces may comprise hook-and-loop fasteners to fasten to each other. In some embodiments, the fastening means 155 of the second strap piece 154b may be overlaid on top of the second strap piece 154b.

In some embodiments, the second strap piece 154b may comprise a series of lumbar supports 160 sewn securely to the second strap piece 154b. These lumbar supports 160 may be elongated strips of a relatively rigid material, such as plastic, wood, metal, and the like. In this embodiment, the pad 102 is worn on the front and the second strap piece 154b wraps around the back at the lumbar region and fastens to the first strap piece 154a. When the stabilizing belt 100 is pulled by the handles 106, the second strap piece 154b does not fold or collapse, but rather, remains firm, thereby providing more comfort and support to the wearer.

In some embodiments, the stabilizing belt 100 further comprises a breathable fabric 156 attached to the interior side 108 of the pad 102. For example, the breathable fabric 156 may be mesh or some other type of lining to provide comfort when the stabilizing belt 100 is worn by the wearer, particularly when worn without clothes.

In some embodiments, as shown in FIG. 4, in addition to or in lieu of the breathable fabric 156, the stabilizing belt 100 may further comprise a rubberized material 158 as the final layer below the pad 102.

Due to the unique design of the stabilizing belt 100, a single belt can be used for various activities. Some stabilizing belts utilize an entire chest harness. Although suitable for watercraft activities, these may be too cumbersome for other activities. The stabilizing belt 100 of the present invention can be used for motorcycle or bicycle riding, watercraft sports, ATV's, snowmobiles, horseback riding, skiing, hiking, walking, sexual activity, medical assistance, therapy, and more.

Figure 8:
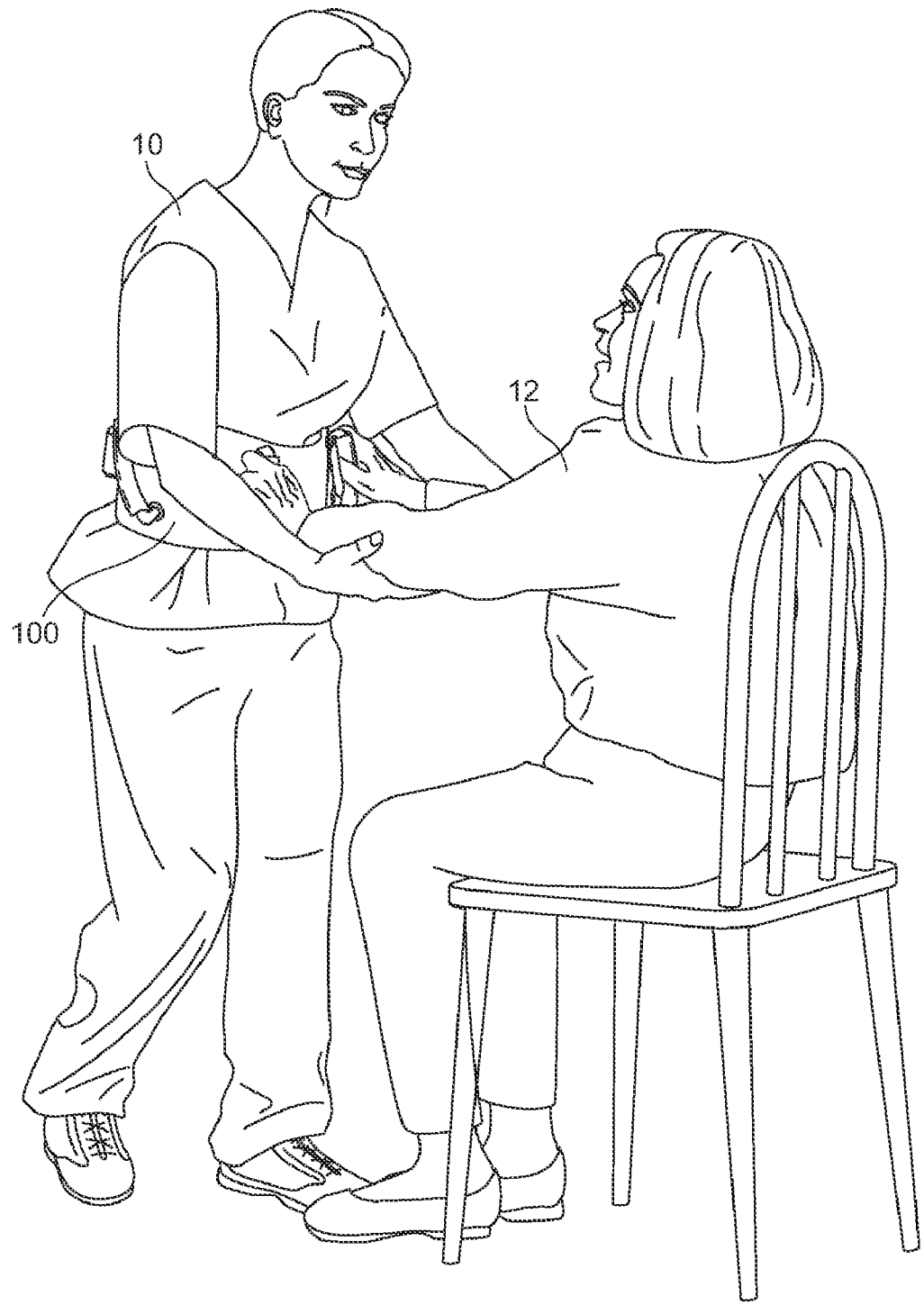
FIG. 8 shows the present invention in use for assisted mobility.

When used for medical assistance, the stabilizing belt 100 may be worn either by the patient (or person requiring assisted mobility) 12 or the caregiver 10. When worn by the caregiver 10, the patient 12 is able to grasp any of the various handles 106a-106d that is most comfortable to the patient 12 and provides the best leverage as shown in FIG. 8. In the meanwhile, the caregiver 10 still has his hands free to utilize them however he wishes.

In some uses, the patient can wear the stabilizing belt 100 and allow the caregiver 10 to lift the patient 12 by any of the handles 106a-106d. In some uses, both the patient 12 and the caregiver 10 can wear the stabilizing belt 100 maximizing the option of having the caregiver hold on to the patient, the patient hold on to the caregiver, or both.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A stabilizing belt, comprising:
   a. a foam pad comprising:
      i. an interior side;
      ii. an exterior side opposite the interior side;
      iii. the interior and exterior sides defining a first edge and a second edge opposite the first edge, the first edge and the second edge having a first width and a second width, respectively; and
      iv. a central region having a third width smaller than the first and second widths;
   b. an elastic strap attached to the first edge of the foam pad;
   c. a fabric strap attached to the second edge of the foam pad, wherein the elastic strap and the fabric strap comprise a fastener to fasten to each other;
   d. a plurality of lumbar supports intermittently spaced apart and secured along the fabric strap;
   e. a rubberized material attached to the interior side of the foam pad;
   f. a nylon belt attached to the exterior side of the foam pad, the nylon belt comprising a first free end and a second free end, the first and second free ends comprising a fastening system to fasten the first and second free ends together;
   g. a plurality of handle supports secured to the foam pad, each handle support comprising a pair of elongated slits through which the nylon belt is interlaced;
   h. a cover having an exterior side and an interior side, wherein the interior side of the cover is overlaid onto the plurality of handle supports and the nylon belt and attached to the exterior side of the foam pad; and
   i. a plurality of handles, each handle attached to one handle support through the cover, each handle comprising a foam grip.

2. The stabilizing belt of claim 1, further comprising a second nylon belt adjacent to the nylon belt, the second nylon belt comprising a second fastening system to facilitate securement of the foam pad to a wearer.

3. A stabilizing belt, comprising:
   a. a pad, comprising:
      i. a first side;
      ii. a second side opposite the first side;
      iii. the first and second sides defining a first edge and a second edge opposite the first edge, the first edge and the second edge having a first width and a second width, respectively; and
      iv. a central region having a third width smaller than the first and second widths;
   b. a belt attached to the pad, the belt comprising a fastening system to secure the pad to a wearer;
   c. a plurality of handle supports attached to the pad;
   d. a plurality of handles attached to the pad, wherein each handle is attached to the pad via one handle support, and
   e. wherein each handle support comprises a pair of elongated slits through which the belt can be interlaced.

4. The stabilizing belt of claim 3, further comprising a plurality of lumbar support members intermittently spaced apart and attached along a strap attached to the pad.

5. The stabilizing belt of claim 3, further comprising a cover having an exterior side and an interior side, wherein the interior side of the cover is overlaid onto the pad.

6. The stabilizing belt of claim 5, wherein the cover comprises:
   a. a slit; and
   b. a pouch attached to the interior side of the cover adjacent to the slit, the pouch being accessible via the slit.

7. The stabilizing belt of claim 3, further comprising a strap attached to the first and second edges of the pad, the strap comprising a fastening means.

8. The stabilizing belt of claim 7, wherein a portion of the strap is elastic.

9. The stabilizing belt of claim 3, further comprising a rubberized material attached to a first side of the pad.

10. A method of a caregiver providing assistance in mobility to a person in need of assisted mobility, the method comprising:
   a. securing a stability belt around the caregiver, the stability belt, comprising:
      i. a pad, comprising a first side; a second side opposite the first side, the first and second sides defining a first edge and a second edge opposite the first edge, the first edge and the second edge having a first width and a second width, respectively; and a central region having a third width smaller than the first and second widths;
      ii. a strap attached to the pad, the strap comprising a first fastener to fasten the pad to the caregiver;
      iii. a belt attached to the pad, the belt comprising a second fastener to secure the pad to the caregiver;
      iv. a plurality of handle supports attached to the pad; and
      v. a plurality of handles attached to the pad, wherein each handle of the plurality of handles is attached to the pad via one handle support;
   b. allowing the person in need of assisted mobility to grasp at least one handle of the plurality of handles; and
   c. moving in a desired direction to mobilize the person in need of assisted mobility.

11. The method of claim 10, wherein the stability belt further comprises a rubberized material attached to the first side of the pad.

12. The method of claim 10, wherein the stability belt further comprises a cover having an exterior side and an interior side, wherein the interior side of the cover is overlaid onto the pad.

13. The method of claim 12, wherein the stabilizing belt comprises a plurality of lumbar support members intermittently spaced apart and secured along the strap.

14. The method of claim 10, wherein a portion of the strap is elastic.

15. A method of receiving assistance in mobility for a person in need of assisted mobility, the method comprising:
  a. securing a stability belt around the person in need of assisted mobility, the stability belt, comprising:
   i. a pad, comprising a first side; a second side opposite the first side, the first and second sides defining a first edge and a second edge opposite the first edge, the first edge and the second edge having a first width and a second width, respectively; and a central region having a third width smaller than the first and second widths;
   ii. a strap attached to the pad, the strap comprising a first fastener to fasten the pad to the person in need of assisted mobility;
   iii. a belt attached to the pad, the belt comprising a second fastener to secure the pad to the person in need of assisted mobility;
   iv. a plurality of handle supports attached to the pad; and
   v. a plurality of handles attached to the pad, wherein each handle of the plurality of handles is attached to the pad via one handle support;
  b. allowing the caregiver to grasp at least one handle of the plurality of handles; and
  c. allowing at least one of the handles to be pulled on to move the person in need of assisted mobility.

16. The method of claim 15, wherein the stabilizing belt further comprises a rubberized material attached to the first side of the pad.

17. The method of claim 15, wherein the stabilizing belt comprises a cover having an exterior side and an interior side, wherein the interior side of the cover is overlaid onto the pad.

18. The method of claim 17, wherein the stabilizing belt comprises a plurality of lumbar support members intermittently spaced apart and secured along the strap.

19. The method of claim 15, wherein a portion of the strap is elastic.

\* \* \* \* \*